United States Patent
Barber et al.

(10) Patent No.: US 9,192,304 B2
(45) Date of Patent: Nov. 24, 2015

(54) APPARATUS AND METHOD FOR ORTHOGONALIZING SIGNALS DETECTING BLOOD OXYGENATION AND BLOOD VOLUME

(76) Inventors: Timothy P. Barber, Boise, ID (US); Mark Changizi, Rensselaer, NY (US)

( * ) Notice: Subject to any disclaimer, the term of this patent is extended or adjusted under 35 U.S.C. 154(b) by 1008 days.

(21) Appl. No.: 12/391,092

(22) Filed: Feb. 23, 2009

(65) Prior Publication Data

US 2012/0277558 A1    Nov. 1, 2012

Related U.S. Application Data

(60) Provisional application No. 61/030,376, filed on Feb. 21, 2008.

(51) Int. Cl.
*A61B 6/00* (2006.01)
*A61B 5/00* (2006.01)
*A61B 5/103* (2006.01)
*A61B 5/1455* (2006.01)
*G01N 21/25* (2006.01)
*G01N 21/29* (2006.01)
*G01N 21/31* (2006.01)

(52) U.S. Cl.
CPC ............. *A61B 5/0075* (2013.01); *A61B 5/1032* (2013.01); *A61B 5/14552* (2013.01); *A61B 5/441* (2013.01); *G01N 21/255* (2013.01); *G01N 21/29* (2013.01); *G01N 2021/3144* (2013.01)

(58) Field of Classification Search
USPC ......... 600/306, 310, 312, 320, 321, 317, 322, 600/323, 324, 326; 359/885, 891
See application file for complete search history.

(56) References Cited

U.S. PATENT DOCUMENTS

| | | | |
|---|---|---|---|
| 3,877,797 A | 4/1975 | Thornton | |
| 4,423,736 A * | 1/1984 | DeWitt et al. | 600/306 |
| 5,218,386 A * | 6/1993 | Levien | 351/163 |
| 5,408,278 A | 4/1995 | Christman | |
| 5,922,246 A | 7/1999 | Matsushita et al. | |
| 7,920,908 B2 * | 4/2011 | Hattery et al. | 600/407 |
| 2001/0005281 A1 * | 6/2001 | Yu | 359/400 |
| 2007/0104472 A1 * | 5/2007 | Quan et al. | 396/79 |
| 2007/0195420 A1 | 8/2007 | Fitchmun | |

OTHER PUBLICATIONS

Changizi et al. ("Bare skin, Blood and the evolution of primate colour vision"; Biol. Lett. 2006 2, Jun. 22, 2006).*
European Patent Office, Examination Report, European Patent Application No. EP 10 251 550.9, Dec. 13, 2012, four pages.
Australian Government IP Australia, Patent Examination Report No. 1, Patent Application No. 2010219290, May 16, 2014, four pages.

* cited by examiner

*Primary Examiner* — Unsu Jung
*Assistant Examiner* — Shahdeep Mohammed
(74) *Attorney, Agent, or Firm* — Fenwick & West LLP

(57) ABSTRACT

A filter for detecting changes in skin color. The filter includes a filter material capable of filtering a frequency range and configured to orthogonalize an overall red response and an overall blue response in response to a spectral power distribution of a given light condition. The overall red response is based on a first plurality of spectral responses for a first human perceived chromatic channel used primarily for detecting blood oxygenation in a human. The overall blue response is based on a second plurality of spectral responses for a second human perceived chromatic channel used primarily for detecting blood volume.

19 Claims, 13 Drawing Sheets

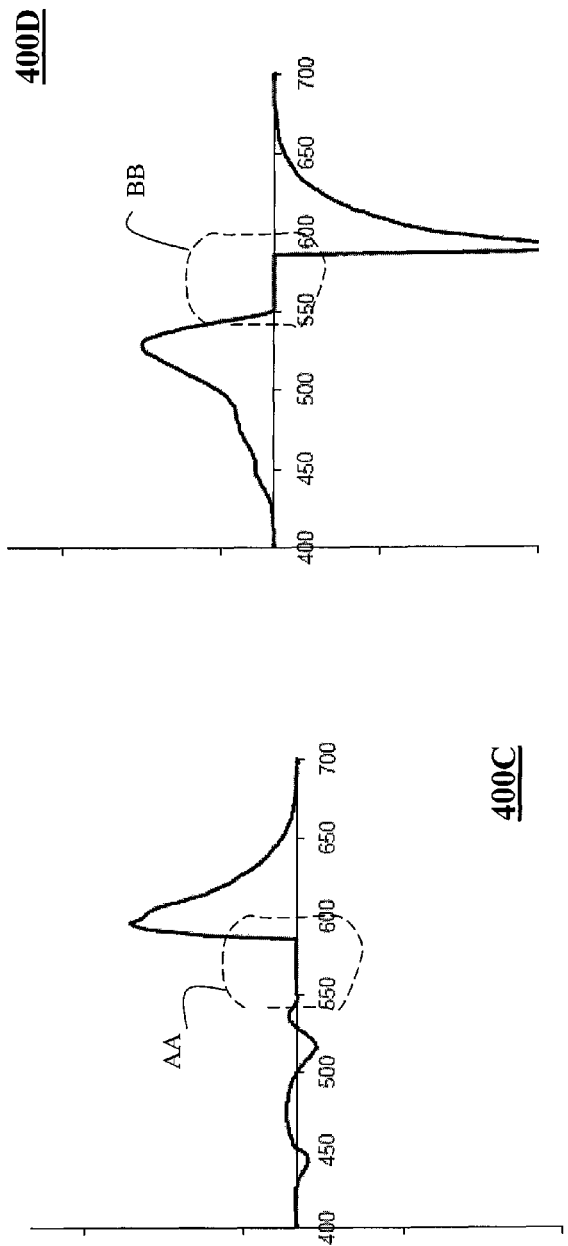

Filtered Frequency Range
(550 – 610 nm) for F12 Illuminant

S - (L+M)
(Blue vs yellow)

L - M
(Red vs green)

865

850

860

855

APPARATUS AND METHOD FOR ORTHOGONALIZING SIGNALS DETECTING BLOOD OXYGENATION AND BLOOD VOLUME

CROSS REFERENCE TO RELATED APPLICATIONS

The present application claims priority to and the benefit of Provisional Application No. 61/030,376 to Timothy P. Barber et al., entitled "Eyepiece Having a Hemo-Notch Filter," filed on Feb. 21, 2008, which is herein incorporated by reference in its entirety.

BACKGROUND OF THE INVENTION

1. Field of the Invention

The present invention pertains to the field of assisted visual perception. Specifically, the present invention provides for a filter, such as a notch filter, that orthogonalizes signals detecting blood oxygen concentration and blood volume through a skin of a human.

2. The Relevant Technology

Color changes in human skin are widely believed to signal emotions such as anger, arousal, fear, and fatigue in humans and all other higher primates. Other similar color changes are indicative of various medical conditions such as hypoxia, cyanosis, jaundice, and also various vasospastic disorders. Recent evidence suggests that the human eye is specially tuned to detect subtle changes in skin color that correspond to changes in blood volume (e.g., signaling anger or some other altered emotional state) and oxygenation of hemoglobin (e.g., signaling jaundice or some other illness). While these changes in color are visible to the unassisted eye, perception of them is in fact severely damped due to a particular range of the visible light spectrum in which the reflectance spectrums of changes in blood volume and oxygenation of hemoglobin is erratic.

SUMMARY OF THE INVENTION

Embodiments of the present invention provide a way to eliminate the damping of our visual response to changes in skin color corresponding to changes in blood volume and blood oxygenation. Specifically, what is described in the present invention is an apparatus and method for detecting changes in blood volume and blood oxygenation by filtering a frequency range of the visible light spectrum in order to orthogonalize human perceived signals detecting changes in blood volume and oxygen concentration.

A filter for detecting changes in skin color is described, in accordance with one embodiment of the present invention. The filter includes a filter material that is capable of filtering a frequency range in the visible light spectrum. The filter material is configured to orthogonalize an overall red response and an overall blue response as perceived by a human in response to a spectral power distribution of a given light condition. The overall red response is based on a first plurality of spectral responses for a first human perceived chromatic channel. The first plurality of spectral responses detects blood oxygenation, or oxygen concentration in hemoglobin, and blood volume as viewed on a skin of a human. The overall blue response is based on a second plurality of spectral responses for a second human perceived chromatic channel. The second plurality of spectral responses also detects blood oxygenation and blood volume.

In another embodiment, a method for detecting changes in skin color is described. The method includes selecting a light condition, wherein the light condition is associated with a spectral power distribution. A first plurality of spectral responses is determined for a first human perceived chromatic channel. The first plurality of spectral responses primarily detects a change in blood oxygen concentration but also picks up signals from blood volume in a skin of a human in response to and as stimulated by the spectral power distribution. A second plurality of spectral responses is determined for a second human perceived chromatic channel. The second plurality of spectral responses primarily detects a change in blood volume but also picks up signals from blood oxygen concentration in response to said spectral power distribution. A frequency range is isolated that filters frequencies in the first and second plurality of spectral responses. The filtering accentuates blood oxygenation with a first perceived color (e.g., red) and the blood volume with a second perceived color (e.g., blue).

In still another embodiment, a method for detecting changes in skin color is described. The method includes receiving a light signal as an input. A frequency range of the light signal is filtered through a filter to generate a modified light signal. The filter orthogonalizes an overall red response indicating a state of oxygenation or a change in blood oxygenation and an overall blue response indicating a state or a change in blood volume in a human. The overall red response is based on a first plurality of spectral responses for a first human perceived chromatic channel. The first plurality of spectral responses primarily detects blood oxygenation but also picks up signals from the blood volume in a skin of a human. The overall blue response is based on a second plurality of spectral responses for a second human perceived chromatic channel. The second plurality of spectral responses primarily detects blood volume but also picks up signals from blood oxygenation. The method includes outputting of a modified light signal from the filter.

BRIEF DESCRIPTION OF THE DRAWINGS

Exemplary embodiments are illustrated in referenced figures of the drawings which illustrate what is regarded as the preferred embodiments presently contemplated. It is intended that the embodiments and figures disclosed herein are to be considered illustrative rather than limiting.

FIG. 4C is a graph illustrating the filtering of the spectral response in FIG. 4A over the L−M channel, in accordance with one embodiment of the present invention.

FIG. 4D is a graph illustrating the filtering of the spectral response in FIG. 4B showing the cancellation of the spectral response indicating a change in blood volume as perceived over the L−M chromatic channel, in accordance with one embodiment of the present invention.

DETAILED DESCRIPTION OF THE PREFERRED EMBODIMENTS

Reference will now be made in detail to the preferred embodiments of the present invention, an apparatus and method for orthogonalizing signals in the visible light spectrum detecting changes in blood oxygenation and blood volume. While the invention will be described in conjunction with the preferred embodiments, it will be understood that they are not intended to limit the invention to these embodiments. On the contrary, the invention is intended to cover alternatives, modifications and equivalents which may be included within the spirit and scope of the invention as defined by the appended claims.

Accordingly, embodiments of the present invention provide a way to eliminate the damping of our visual response to changes in skin color corresponding to changes in blood volume or blood oxygenation. As a result, in embodiments of the invention, perceived signals are orthogonalized such that an overall red response in a first chromatic channel indicates a change in blood oxygenation and an overall blue response in a second chromatic channel indicates a change in blood volume when viewing skin of a human.

The term "blood oxygenation" is intended to describe the oxygen concentration or saturation in blood from hemoglobin. Hemoglobin is used to transport oxygen in the blood of vertebrates. Hemoglobin saturation leaving the lungs is about 98-99% saturated with oxygen in a healthy human. Deoxygenated blood returning to the lungs is about 75% saturated. As such, an increase in blood oxygenation implies an increase in oxygen concentration in hemoglobin in the blood. Also, a decrease in blood oxygenation implies a decrease in oxygen concentration in hemoglobin in blood.

While embodiments of the present invention are described that orthogonalize perceived signals detecting blood oxygenation and blood volume, other embodiments are well suited to orthogonalizing perceived signals detecting other physical states, physiological states, or conditions.

Figure 1:
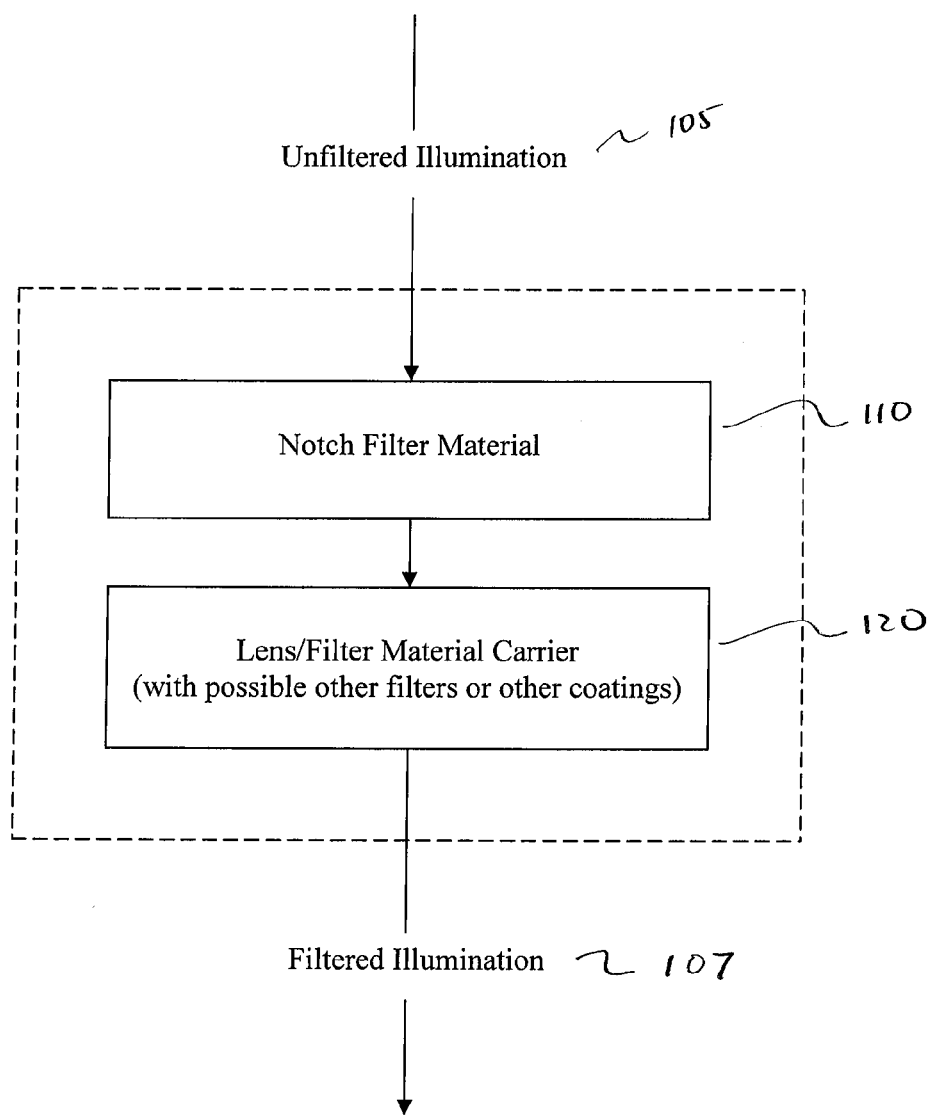
FIG. 1 is a block diagram of an apparatus that is capable of filtering signals in the visible light spectrum to orthogonalize signals detecting changes in blood oxygenation and blood volume, in accordance with one embodiment of the present invention.

FIG. 1 is a block diagram of a filter 100 that is capable of filtering signals in the visible light spectrum to orthogonalize human perceived signals detecting changes in blood oxygenation and blood volume, in accordance with one embodiment of the present invention. As shown, an input signal 105 is characterized by unfiltered illumination associated with a given light condition. Filter 100 filters the input signal 105 and generates an output signal 107 that is filtered illumination. The filter 100 is capable of detecting changes in skin color to accentuate changes in oxygen concentration in hemoglobin and blood volume.

In particular, the filter 100 includes a filter material 110 that is capable of filtering a specific narrow frequency range of visible light. The filtered range can be referred to as the problematic band in which conflicting signals indicate a wrongly perceived color when viewed by a human, especially when trying to detect changes in oxygen concentration in hemoglobin and blood volume.

Physiologically, light energy corresponding to light wavelengths stimulates eye photoreceptors. These photoreceptors include cones that respond mainly to bright light conditions and rods that respond to low light conditions. Color sensitivity is provided mainly from the cones, which can be further classified as being L-cones (sensitive to long wavelengths), M-cones (sensitive to medium wavelengths), and S-cones (sensitive to short wavelengths. Combinations of the various stimuli as provided by the cones are processed by the brain to produce various perceptions of color. As such, the spectral responses approximate the perceived color by a human under certain skin conditions (e.g., changes in oxygen concentration in hemoglobin, blood volume, etc.).

The problematic band within the spectral responses may indicate confusing signals processed by the brain to indicate a wrong color. For instance, diminishing redness may wrongly indicate to the brain a slight blue color. Also, a diminishing blueness may wrongly indicate to the brain a slight yellow color. Generally, redness is an indication of oxygen concentration in hemoglobin contained in blood. The more red that is perceived indicates increased oxygen concentrations. Also, blueness is an indication of blood volume. The more blue that is perceived indicates increased blood volume. As such, due to contributions from the problematic band, for example diminishing redness, that indicates a lower concentration of oxygen from hemoglobin, may trigger a perceived blueness, which falsely indicates a level of blood volume. Embodiments of the present invention are able to filter out the problematic band so that perceived signals in the brain clearly accentuate colors that indicate changes in oxygen concentration in hemoglobin and blood volume.

Specifically, the filter material 110 is configured to orthogonalize an overall red response and an overall blue response in response to a spectral power distribution of a given light condition. The filtered frequency range is designed for a given light condition, such as those approximating natural light, or various other artificially created lighting conditions generated from incandescent, fluorescent, halogen, or other lights. By filtering out the problematic band, the spectral responses in the brain are orthogonalized, such that an overall redness corresponds to oxygen concentration in hemoglobin and overall blueness corresponds to blood volume, while minimizing any interference between the two.

The overall red response is based on a first plurality of spectral responses for a first human perceived chromatic channel. For instance, the first chromatic channel is the L−M signal obtained by subtracting the signal from the M-cones from the L-cones. The spectral responses primarily reflect oxygen concentration in hemoglobin, but also picks up signals from a state or changes in blood volume, as perceived by a human. That is, the spectral responses approximate the colors perceived by a human when viewing a particular skin condition (e.g., change in oxygen concentration in hemoglobin, change in blood volume, etc.).

Also, the overall blue response is based on a second plurality of spectral responses for a second human perceived chromatic channel. For instance, the second chromatic channel is the S−(L+M) signal obtained by subtracting from the signal from the S-cones the combination of signals from the M-cones and L-cones. The spectral responses primarily reflect blood volume, but also picks up signals reflecting an oxygenation state or a change in oxygen concentration in hemoglobin, as perceived by a human. That is, the spectral responses approximate the colors perceived by a human when viewing a particular skin condition (e.g., change in oxygen concentration in hemoglobin, change in blood volume, etc.).

In one embodiment, the filter material 110 comprises a notch filter. In particular, the notch filter that passes all frequencies except for a defined set of frequencies, such as a stop band of frequencies that is centered around a center frequency. A notch filter is capable of filtering out the problematic band of frequencies to accentuate the colors indicating changes in oxygen concentration in hemoglobin and blood volume.

As shown in FIG. 1, carrier 120 is included within the filter 100, in one embodiment. The carrier provides a medium through which the filter material 110 may operate. More generally, the carrier 120 may be any substance that is combined with the filter material 110. In one embodiment, the filter material 110 is fully or partially incorporated into the carrier 120. For instance, the filter material 110 may be impregnated into the carrier 1220. In another embodiment, the filter material 110 is layered on the carrier 120, such as when layering on a substrate. In one case, the filter material 110 is adjacent to the carrier 120.

For instance, carrier 120 may comprise a lens material. The lens material may be of any type (e.g., non-prescription, prescription, etc.). As examples, the lens material may be used in conjunction with an eyepiece, eyeglasses, safety glasses, etc. The use of the term "eyepiece" is intended to encompass any eyewear, and so encompasses a single lens used for aiding vision (e.g., eyeglasses, contact lenses, visors, etc.). In addition, the lens material may be used in conjunction with any other suitable device, such as a camera, or imaging device, etc.

Also, carrier 120 may be characterized as a coating that is then put on other substances. When combined with the filter material 110, the coating may absorb the desired frequency range corresponding to the problematic band. In addition, when combined with the filter material 110, the coating may reflect the desired frequency range corresponding to the problematic band. For instance, the coating may be applied to the outside surface of various types of lighting mechanisms (e.g., light bulbs, fluorescent tubes, etc.). Also, the coating may be applied to a lens material, or any other type of material. In one case, the coating comprises light-absorbing molecules to absorb the desired frequency range corresponding to the problematic band. In another case, the coating reflects the frequency range of light.

In one embodiment, the filter 100 may appear as a tint. The tint is applied to glass, polycarbonate, or any other suitable substrate in a uniform manner. Various techniques may be used for tinting. For example, a constant density process may be used to tint the carrier 120 with the filter material 110. In another example, the tint is applied through an immersion process. Specifically, to tint a polycarbonate (plastic) lens, the lens is immersed in a special liquid or substance containing the tinting material. The tint is slowly absorbed into the polycarbonate. To make a darker tint, the lens is left in the liquid for a longer period. As such, the tint is built into the lens during manufacturing.

In one implementation, a user having aided vision from embodiments of the present invention can view the skin of another person and more easily detect changes in skin conditions, such as blood volume and oxygen concentration in hemoglobin (oxygenation). Moreover, embodiments of the present invention aid the user in distinguishing between blood volume and oxygenation. In particular, because the problematic band is blocked, the filter orthogonalizes human perception of blood volume compared to the human perception of oxygenation, minimizing interference between the two perceptions. For instance, a user is able to detect changes in blood volume from a perceived degree of blueness (e.g., an increase in blood volume is a perceived increase in blueness), and is able to detect changes in oxygenation of hemoglobin from a perceived degree of redness (e.g., an increase in oxygenation from hemoglobin is a perceived increase in redness).

In one implementation, depending on the circumstances, the perceived color can be related to either a change in the emotional state of the viewed person, or a change in the health of the viewed person. In other words, the same perceived color may indicate two different things, and context may then be used to distinguish. For example, if a person is playing poker, the perceived skin color may signal that the person is lying, i.e. bluffing. But if the person is a patient in a hospital, the same color may indicate that it is more likely that the health of the person has changed, and not that the emotional state of the person has temporarily changed. Another way to distinguish between changes in emotional state and changes in health is of course the duration of the change in the perceived skin color. If the change persists, it more likely signals a change in health.

Figure 2:
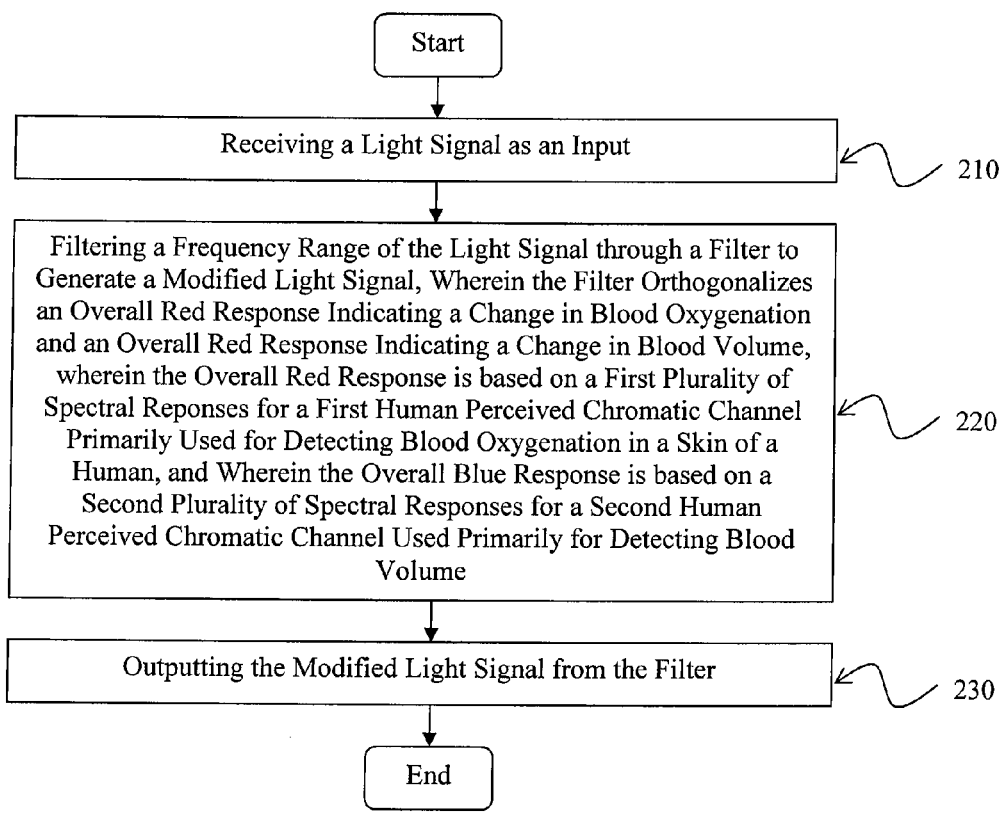
FIG. 2 is a flow diagram illustrating a method for filtering signals to detect changes in blood oxygenation and blood volume, in accordance with one embodiment of the present invention.

Now turning to FIG. 2, a flow diagram 200 illustrates a method for detecting changes in skin color, in accordance with one embodiment of the present invention. The method of flow diagram 200 implements the filter 100 of FIG. 1 used for orthogonalizing signals used for detecting blood oxygenation and blood volume. The method includes receiving a light signal as an input.

At 210, a light signal is received as an input. For instance, in FIG. 1, unfiltered illumination 105 is received by the filter 100. As examples, the light signal is received by a filter (e.g., eyeglass lens, camera lens, protective covering, coating, etc.).

At 220, a frequency range of the light signal is filtered through a filter to generate a modified light signal. For instance, in FIG. 1, unfiltered illumination 105 is passed through filter 100. The filter orthogonalizes an overall red response indicating a change in blood oxygenation and an overall blue response indicating a change in blood volume in a human. The overall red response is based on a first plurality of spectral responses for a first human perceived chromatic channel, as will be more fully described below. The first plurality of spectral responses is primarily used to detect states, or a change in the blood oxygenation, but also may pick up responses from the blood volume in a skin of a human. The overall blue response is based on a second plurality of spectral responses for a second human perceived chromatic channel. The second plurality of spectral responses is primarily used to detect states, or changes in blood volume, but may pick up responses from blood oxygenation, as will be more fully described below.

At 230, the modified light signal is outputted from the filter. In this manner, signals detecting blood oxygenation and blood volume are orthogonalized. As such, an overall red response is indicative of blood oxygenation and an overall blue response is indicative of blood volume, as will be more fully described below.

Figure 3:
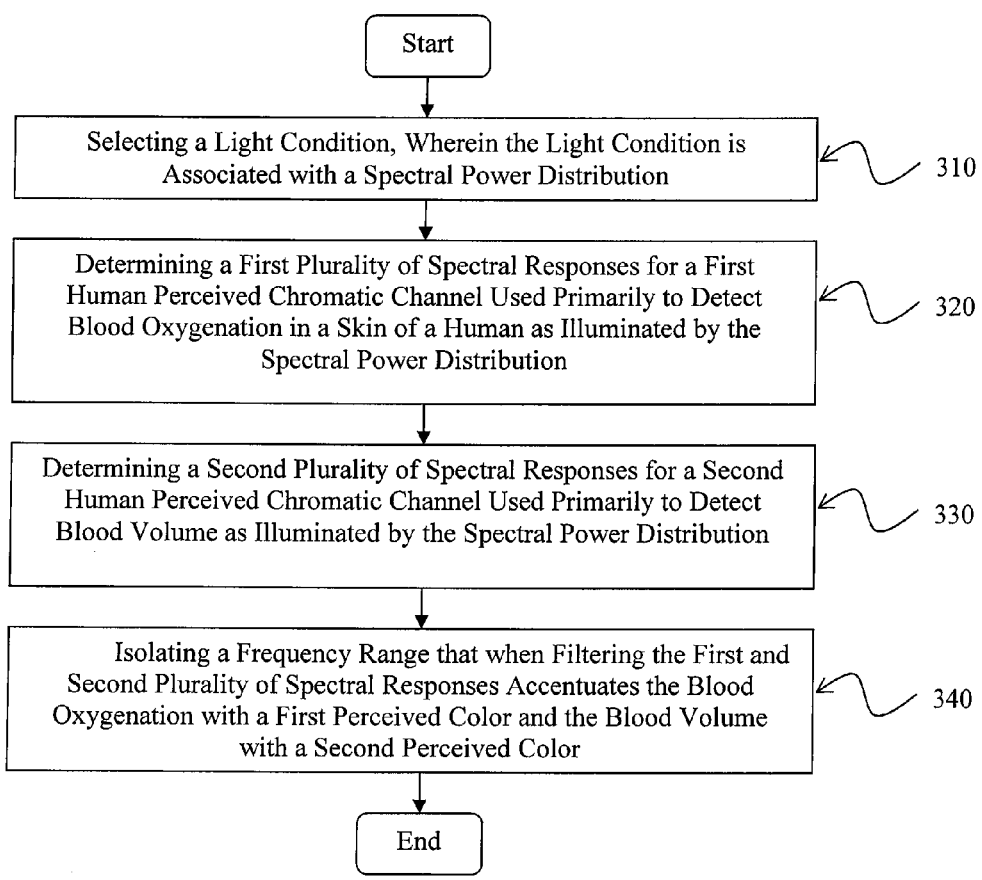
FIG. 3, is a flow diagram illustrating a method for orthogonalizing an overall red response indicating a change in blood oxygenation and an overall blue response indicating a change in blood volume, in accordance with one embodiment of the present invention.

FIG. 3 is a flow diagram 300 illustrating a method for detecting changes in skin color, and more particularly, changes in blood oxygenation and blood volume, in accordance with one embodiment of the present invention. Specifically, the method is able to determine a frequency range that is blocked in order to accentuate blood oxygenation and blood volume in a skin of a person. In one embodiment, the method of FIG. 3 is implemented with the filter 100 of FIG. 1.

At 310, a light condition is selected. The light condition is associated with a spectral power distribution. The light condition approximates an environment in which embodiments of the invention operate. Given that different light conditions may affect the various perceived spectral responses received in the brain of a human, the resulting frequency range that is masked or blocked depends on the light condition selected.

The light condition is associated with a spectral power distribution. That is, a given light condition includes different wavelengths of illumination, and each wavelength is associated with a corresponding power. As such, the spectral power distribution describes the frequencies over which that light condition illuminates a spectrum, such as those within the visible spectrum. For a given spectral power distribution, contributions to the overall illumination of that light condition is described for each wavelength. For instance, more power may be given to a particular frequency or range of frequencies. That is, more illumination is provided at that frequency or range of frequencies for a given spectral power distribution.

Figure 7A:
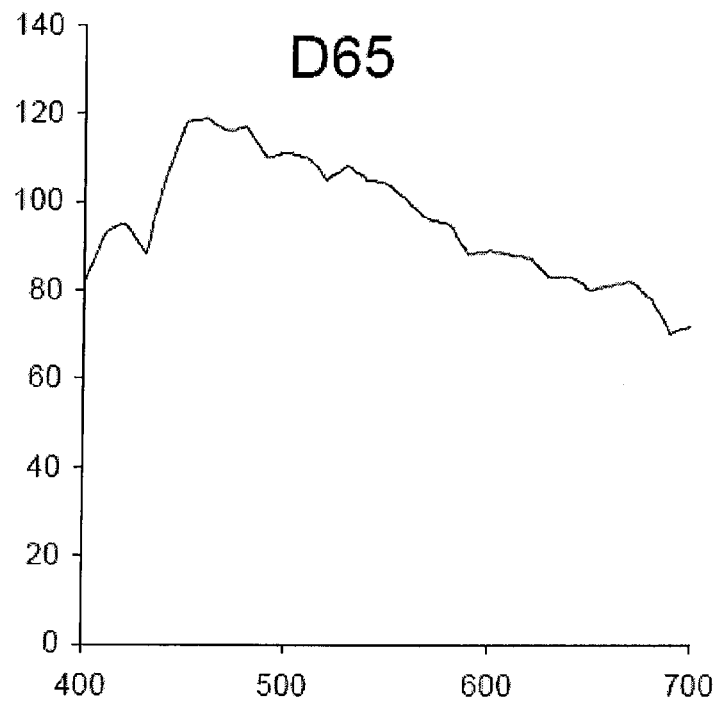
FIG. 7A is a graph illustrating a spectral power distribution for the D65 standard illuminant for wavelengths between 400 and 700 nanometers (nm), in accordance with one embodiment of the present invention.

In one case, the light condition approximates that of a given illuminant. For instance, the light condition may be represented by the D65 standard illuminant approximating a natural light condition. For example, FIG. 7A is a graph illustrating a spectral power distribution for the D65 standard illuminant for wavelengths between 400 and 700 nm. D65 is the most popular standard illuminant defined by the International Commission on Illumination (CIE). It is part of the D series of illuminants that try to portray standard illumination conditions at open air in different parts of the world. D65 corresponds roughly to a midday sun in Western/Northern Europe, hence it is also called a daylight illuminant. More particularly, the CIE 1931 color space chromaticity coordinates of D65 are x=0.31271, y=0.32902 using the CIE 1931 standard colorimetric observer and x=0.31382, y=0.33100 using the CIE 1964 calorimetric observer. These correspond to a correlated color temperature of 6504 K. Rec. 709, used in HDTV systems, truncates the CIE 1931 coordinates to x=0.3127, y=0.3290. As any standard illuminant is represented as a table of calorimetric average data, any light source which statistically has the same spectral power distribution can be considered a D65 light source.

In another case, the natural light condition is represented by the F series of illuminants that represent various types of fluorescent lighting. As such, embodiments of the present invention are able to orthogonalize the spectral responses in the brain to accentuate blood oxygenation and blood volume for an environment (e.g., indoor or outdoor) that is illuminated with a particular fluorescent lighting. In one implementation, the given light condition is represented by the F1 standard illuminant. In another implementation, the given light condition is represented by the F12 standard illuminant.

In still another embodiment, the given light condition may be a combination of one or more standard illuminants. That is, the given light condition approximates one or more defined light conditions. As such, the frequency range that is filtered is selected for use under one or more defined light conditions. For instance, the frequency range is suitable for use under fluorescent lighting and under natural light conditions. In this case, the frequency range that is filtered enables the orthogonalization of perceived signals in the visible light spectrum detecting changes in blood oxygenation and blood volume.

While embodiments of the present invention are described using particular light conditions for illustration, it intended that the invention is not limited to those light conditions described. That is, embodiments of the present invention are suitable for masking out frequencies in a corresponding problematic band for any given light condition, or combination of light conditions for use in orthogonalizing signals detecting blood oxygenation and blood volume.

Returning back to FIG. 3, at 320, a first plurality of spectral responses is determined for a first human perceived chromatic channel, as illuminated, or in response to, the spectral power distribution of the given light condition. More specifically, the spectral responses are approximations of what wavelengths the brain receives for a particular skin condition, in one embodiment. In one skin condition, a first spectral response is for high oxygenation of the blood. In another skin condition, a second spectral response is for high blood volume.

For instance, the first human perceived chromatic channel is determined from the L-cones and the M-cones. More particularly, the chromatic channel is determined from the difference between the signals from the L-cones and the M-cones, or the L–M channel. The first chromatic channel is used to determine the difference between redness and greenness and can be used to detect blood oxygenation. It is determined that high oxygenation corresponds to a redness in the blood, whereas lower oxygenation corresponds to less redness and more greenness in the blood. The L–M difference determined from signals from the L-cones and the M-cones serves as a channel for perceiving redness and greenness, which are opposites in this chromatic channel.

Further, by taking the difference between signals from the L-cones and the M-cones, variability in skin color is at least partially cancelled out in the L−M signal. That is, varying degrees of yellow corresponding to various shades of skin color stimulate the L-cones and the M-cones, and are at least partially canceled out when subtracting the M signal from the L-signal.

Various skin conditions can be targeted to determine corresponding spectral responses in the first human perceived chromatic channel. For instance, conditions can include degrees of blood oxygenation as exhibited by skin, and more particularly when blood oxygenation is high. In addition, conditions can include degrees of blood volume as exhibited by skin, and more particularly, when blood volume is high.

Figures 4A, 4B:
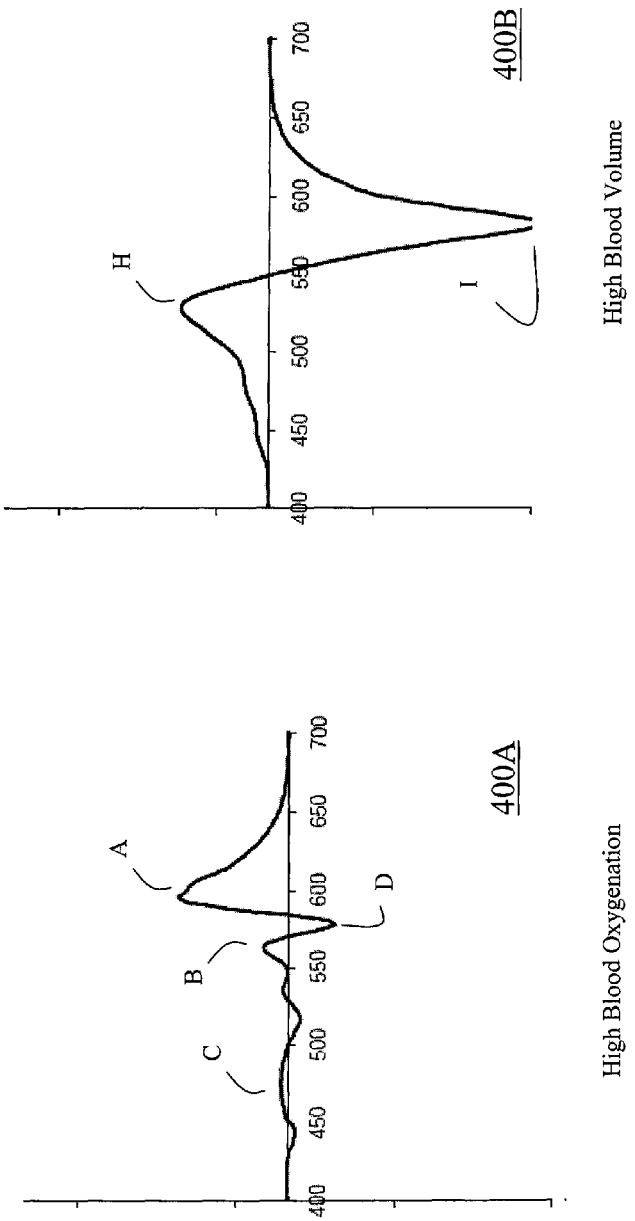
FIG. 4A is a graph illustrating an unfiltered spectral response over the L-M chromatic channel that is perceived by a human indicating a change in blood oxygenation, in accordance with one embodiment of the present invention.
FIG. 4B is a graph illustrating an unfiltered spectral response over the L-M chromatic channel that is perceived by a human indicating a change in blood volume, in accordance with one embodiment of the present invention.

FIGS. 4A and 4B are graphs illustrating the unfiltered spectral responses or signatures for high blood oxygenation and high blood volume in a skin of a human as perceived in the first chromatic channel. The spectral responses are in association with a given light condition, in this case that approximated by the D65 standard illuminant. In addition, the spectral responses are associated with particular skin conditions that provide interfering signals to the brain. For instance, in the case where there is high blood oxygenation combined with high blood volume, there may be interfering signals that reduces the overall red response associated with the high blood oxygenation.

For instance, FIG. 4A illustrates the approximate spectral response 400A as perceived by a human for skin exhibiting high blood oxygenation. The spectral response 400A is unfiltered and is determined in the first human perceived chromatic channel (e.g., L−M). As expected, since red skin typically indicates high blood oxygenation, there is a high red response given the area above the x-axis corresponding to peaks A, B and C. In addition, there is a slight green response given the area below the x-axis at peak D at approximately 550 nm that is present for skin exhibiting high blood oxygenation. The slight greenness of the spectral response may slightly interfere with the overall redness perceived by the brain to falsely indicate less blood oxygenation. Embodiments of the present invention are able to cancel out at least some of interference due to the green response in spectral response 400A, as will be described below in connection with FIG. 4C.

FIG. 4B illustrates the approximate spectral response 400B as perceived by a human for skin exhibiting high blood volume. While skin exhibiting high blood volume is typically blue, there is a spectral signature in the L−M chromatic channel that may interfere with the perceived redness that is used to detect changes in blood oxygenation, and especially for skin exhibiting high blood oxygenation. Specifically, there is both a red response given the area above the x-axis corresponding to peak H at approximately 525 nm, and a more prominent green response given the area below the x-axis corresponding to peak I at approximately 580 nm. As such, the overall greenness perceived by the brain from spectral response 400B may interfere with the overall redness from spectral response 400A indicating high blood oxygenation. Embodiments of the present invention are able to balance the contributions of perceived redness and greenness from the spectral response 400B that is present for skin exhibiting high blood volume, and cancel the interfering effect of the spectral response 400B, as will be described below in connection with FIG. 4D.

Returning back to FIG. 3, at 330, a second plurality of spectral responses is determined for a second human perceived chromatic channel, as illuminated, or in response to, the spectral power distribution of the given light condition. More specifically, the spectral responses are approximations of what wavelengths the brain receives for one or more skin conditions. As described above, in one skin condition, a first spectral response is for high oxygenation of the blood. In another skin condition, a second spectral response is for high blood volume.

For instance, the second human perceived chromatic channel is determined from S-cones, L-cones, and M-cones. More particularly, the second chromatic channel is determined from the difference between the signals from the S-cones and the combination of the signals from L-cones and M-cones, or the S+(L+M) channel. The second chromatic channel is used to determine the difference between blueness and yellowness and can be primarily used to detect blood volume. It is determined that high blood volume corresponds to a blueness in the blood, whereas a lower blood volume corresponds to less blueness and more yellowness in the blood. S-cones are primarily used to detect blueness, and both the L-cones and M-cones are primarily used to detect yellowness. As such, the S−(L+M) chromatic channel illustrates a blueness vs. yellowness in a spectral response for a given skin condition.

Various skin conditions can be targeted to determine corresponding spectral responses in the second human perceived chromatic channel. For instance, conditions can include degrees of blood volume as exhibited by skin, and more particularly, when blood volume is high. In the second chromatic channel, other secondary conditions can include degrees of blood oxygenation as exhibited by skin, and more particularly when blood oxygenation is high. As described before, these secondary conditions may provide signals that interfere with and confuse the perception of blueness that is used for detection of degrees of blood volume.

Figure 5A:
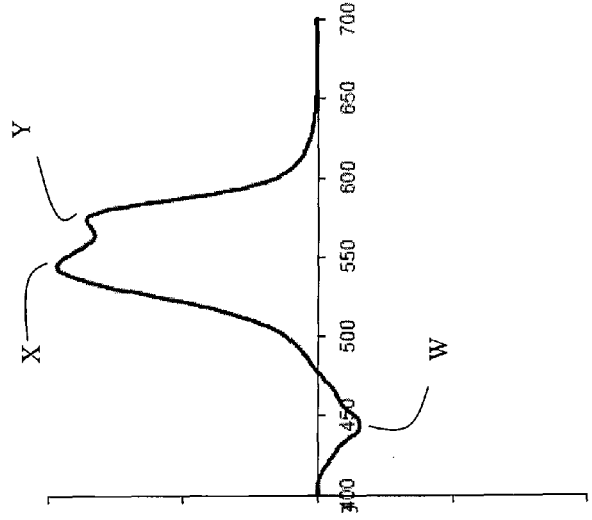
FIG. 5A is a graph illustrating an unfiltered spectral response over the S−(L+M) chromatic channel that is perceived by a human indicating a change in blood oxygenation, in accordance with one embodiment of the present invention.
Figure 5B:
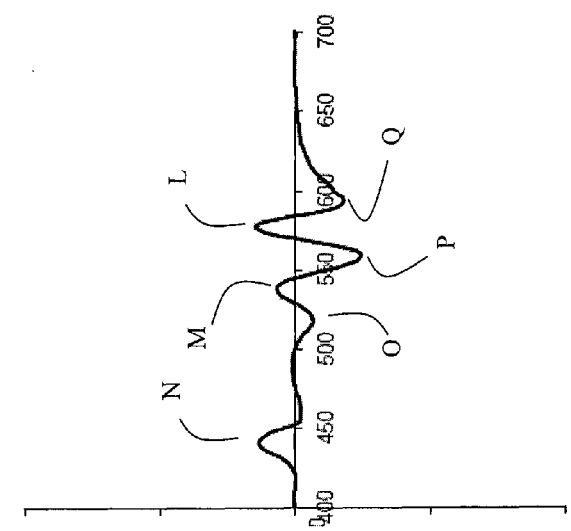
FIG. 5B is a graph illustrating an unfiltered spectral response over the S−(L+M) chromatic channel that is perceived by a human indicating a change in blood volume, in accordance with one embodiment of the present invention.

FIGS. 5A and 5B are graphs illustrating the unfiltered spectral responses or signatures for high blood oxygenation and high blood volume in a skin of a human, as perceived in the second chromatic channel. The spectral responses are in association with a given light condition, in this case that approximated by the D65 standard illuminant. In addition, the spectral responses are associated with particular skin conditions that provide interfering signals to the brain. For instance, in the case where there is high blood volume combined with high blood oxygenation, there may be interfering signals that reduces the overall blue response associated with the high blood volume.

Looking first at FIG. 5B, illustrated is an approximate spectral response 500B as perceived by a human for skin exhibiting high blood volume. The spectral response 500B is unfiltered and is determined in the second human perceived chromatic channel (e.g., S−(L+M)). As expected, since blue skin typically indicates high blood volume, there is a high blue response given the area above the x-axis corresponding to peaks X and Y. In addition, there is a slight yellow response given the area below the x-axis at peak W at approximately 440 nm that is present for skin exhibiting high blood volume. The slight yellowness of the spectral response may slightly interfere with the overall blueness perceived by the brain to falsely indicate less blood volume. As shown, this interference is slight in comparison with the large blue signature.

Now turning to FIG. 5A, illustrated is an approximate spectral response 500A as perceived by a human for skin exhibiting high blood oxygenation. While skin exhibiting high blood oxygenation is typically red, there is a spectral signature in the S−(L+M) chromatic channel that may interfere with the perceived blueness that is used to detect changes in blood volume, and especially for skin exhibiting high blood volume. Specifically, as shown in FIG. 5A, there is both a blue response given the area above the x-axis corresponding to peaks L, M, and N, and a more prominent yellow response given the area below the x-axis corresponding to peaks O, P and Q. As such, the overall yellowness perceived by the brain from spectral response 500A may interfere with the overall blueness from spectral response 500B used to detect high blood volume. Embodiments of the present invention are able to balance the contributions of perceived blueness and yellowness from the spectral response 500A that is present for skin exhibiting high blood oxygenation, and cancel the interfering effect of the spectral response 500A, as will be described below in connection with FIG. 5C.

Figure 6A:
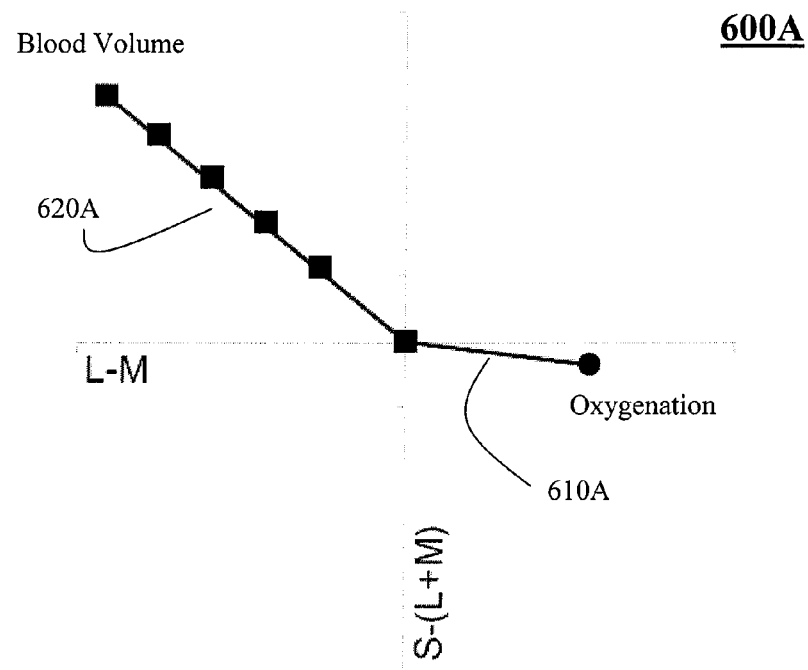
FIG. 6A is a vector graph illustrating the lack of orthogonality of signals indicating blood oxygenation and blood volume without any filtration of the visible light spectrum, in accordance with one embodiment of the present invention.

FIG. 6A is a graph 600A showing vectors illustrating the overall color effect for the spectrum responses used to detect both blood oxygenation and blood volume over the first (L−M) channel and the second chromatic channel [S−(L+M)]. The horizontal axis is used to show the red vs. green response over the first chromatic channel (L−M), where redness is associated with the right side and greenness is associated with the left side of the horizontal axis. The vertical axis is used to show the blue vs. yellow response over the second chromatic channel [S−(L+M)], where blueness is associated with the top portion and yellowness is associated with the bottom portion of the vertical axis.

For instance, vector 610A is representative of the perceived response for high blood oxygenation that is unfiltered. Typically, human perception associates a strong red response with high blood oxygenation. As shown in FIG. 6A, vector 610A mostly shows a weak red signal, as evidenced from FIGS. 4A and 4B. That is, the length of vector 610A indicates that there is strong influence from greenness from the area under peak I, shown in FIG. 4B, thereby weakening the overall red response. In addition, there is a slight yellow signal leaking through, pulling vector 610 below the horizontal axis, further weakening the red response and possibly introducing confusion, as shown in FIG. 5A.

Vector 620A is representative of the perceived response for high blood volume that is unfiltered. Typically, human perception associates a strong blue response with high blood volume. As shown in FIG. 6A, vector 620A shows a signal that is mixed with blueness and greenness. The strength of the blue signal is shown in FIGS. 5A and 5B in the S−(L+M) chromatic channel. In particular, the area under peaks X and Y produces a large overall blue response. However, there is also a strong influence of greenness in the L−M channel from the area under peak I shown in FIG. 4B, pulling vector 620A away from the vertical axis and thereby weakening the blue response.

More particularly, vectors 610A and 620A are not orthogonal. For instance, the two vectors are not ninety degrees from each other. This indicates that signals used for detecting blood volume in vector 620A may interfere and confuse the brain when detecting blood oxygenation using vector 610A. Likewise, signals used for detecting blood oxygenation in vector 610A may interfere and confuse the brain when detecting blood volume using vector 620A.

Figure 7B:
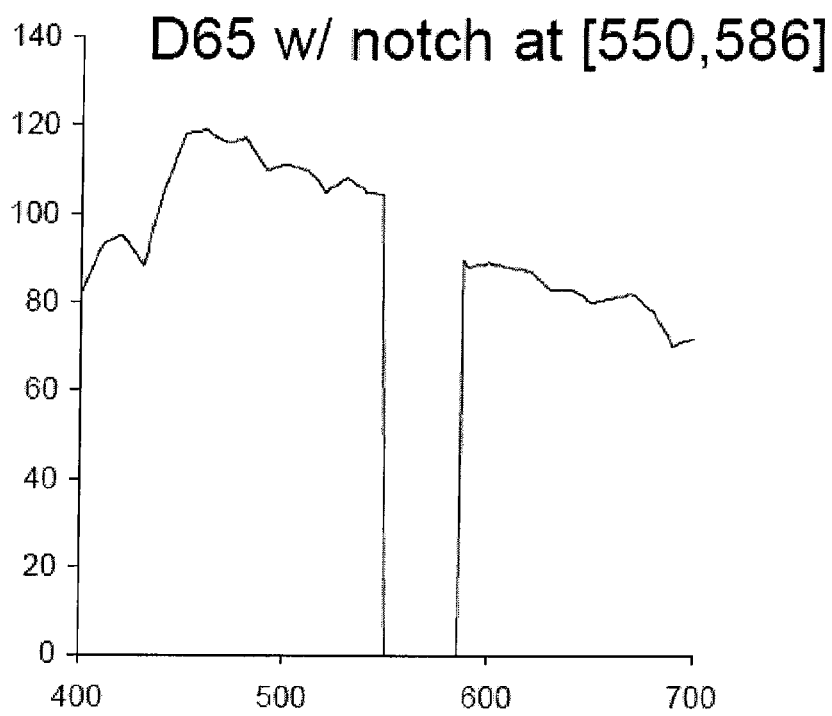
FIG. 7B is a graph illustrating a spectral power distribution for the D65 standard illuminant of FIG. 7A that is filtered between 550-586 nm, in accordance with one embodiment of the present invention.

Returning now back to flow diagram 300, at 340, a frequency range is isolated for filtering. More particularly, the frequency range is blocked or filtered to prevent those frequencies from reaching the brain. In one embodiment, the frequency range is filtered at the illumination source, thereby preventing those frequencies from being present. As such, those frequencies are blocked from reaching and stimulating the visual cortex associated with the human eye that is used for color determination. For example, FIG. 7B is a graph illustrating a spectral power distribution that is filtered between 550-586 nm for the D65 standard illuminant for wavelengths between 400 and 700 nanometers (nm). In another embodiment, the frequency range filters wavelengths in the visible spectrum before reaching the visual cortex (e.g., in eyeglasses). As such, those frequencies are again blocked from reaching and stimulating the visual cortex.

Filtering the frequency range blocks out the problematic band, previously described. More particularly, the frequency range is ultimately filtered in the first and second plurality of spectral responses. As a result, the first and second plurality of spectral responses accentuates the blood oxygenation with a first perceived color (e.g., redness) and accentuates blood volume with a second perceived color (blueness). That is, the overall response (e.g., redness) in the first chromatic channel used for detecting blood oxygenation is orthogonal to the overall response (e.g., blueness) in the second chromatic channel used for detecting blood volume. Interference is minimized between signals from spectral responses in the first chromatic channel and spectral responses in the second chromatic channel.

FIGS. 4C and 4D are graphs illustrating the filtered spectral responses or signatures of FIGS. 4A and 4B for high blood oxygenation and high blood volume in a skin of a human as perceived in the first human perceived chromatic channel (e.g., L−M). As previously described, the L−M chromatic channel produces an overall response that can be used to detect blood oxygenation. For instance, the overall response indicates a redness that is perceived by the brain to indicate varying degrees of blood oxygenation.

More particularly, FIG. 4C illustrates the approximate spectral response 400C as perceived by a human for skin exhibiting high blood oxygenation. The spectral response in 400C is filtered and determined in the first chromatic channel (e.g., L−M). Previously, in FIG. 4A, mostly at peak D, there is a green response that may interfere with the overall redness produced by the spectral response. By selecting the appropriate frequency range, the overall green response may be filtered out and minimized, thereby removing any interference with the overall red response by the green response from peak D. As shown in highlighted area AA of FIG. 4C, a frequency range between 550-586 nm is selected for filtering, and removes the green response previously shown in FIG. 4A. The selected frequency range orthogonalizes signals for detecting blood oxygenation and blood volume, as will be described below.

In addition, the overall response in the first chromatic channel (e.g., L−M) may be interfered by signals present in association with the detection of blood volume. FIG. 4D illustrates the approximate spectral response 400D as perceived by a human for skin exhibiting high blood volume. The spectral response 400D is filtered and determined in the first chromatic channel. Previously, in FIG. 4B, at peak I, the green response dominates and may interfere with the overall red response perceived by the brain in the first chromatic channel. The present invention is able to reduce the influence of the spectral response 400D that is generated from the presence of blood volume in the first chromatic channel. As such, the overall response in the first chromatic channel (L−M) is used primarily to detect blood oxygenation with minimal interference from signals associated with detection of blood volume.

In FIG. 4D, by selecting the appropriate frequency range, the spectral response 400D is balanced through the removal of part of the curve associated with peak I in FIG. 4B. That is, the area above the horizontal axis is approximately equal to the area below the horizontal axis, and thereby minimizing any effect the spectral response 400D may have on the brain when processing the overall response in the first chromatic channel (L−M). As shown in highlighted area BB of FIG. 4D, the selected frequency range between 550-586 nm is filtered out, thereby balancing the spectral response 400D and minimizing its effect on the overall red response in the first chromatic channel. In other words, the signals from the first chromatic channel generate primarily an overall red response that is attributed mostly to blood oxygenation. That is, the overall response is generated from the spectral response in FIG. 4C used for detecting blood oxygenation, with minimal interference from signals associated with detecting blood volume in FIG. 4D. In that manner, an overall red response used to detect changes in blood oxygenation is orthogonalized from signals detecting blood volume.

Figures 5C, 5D:
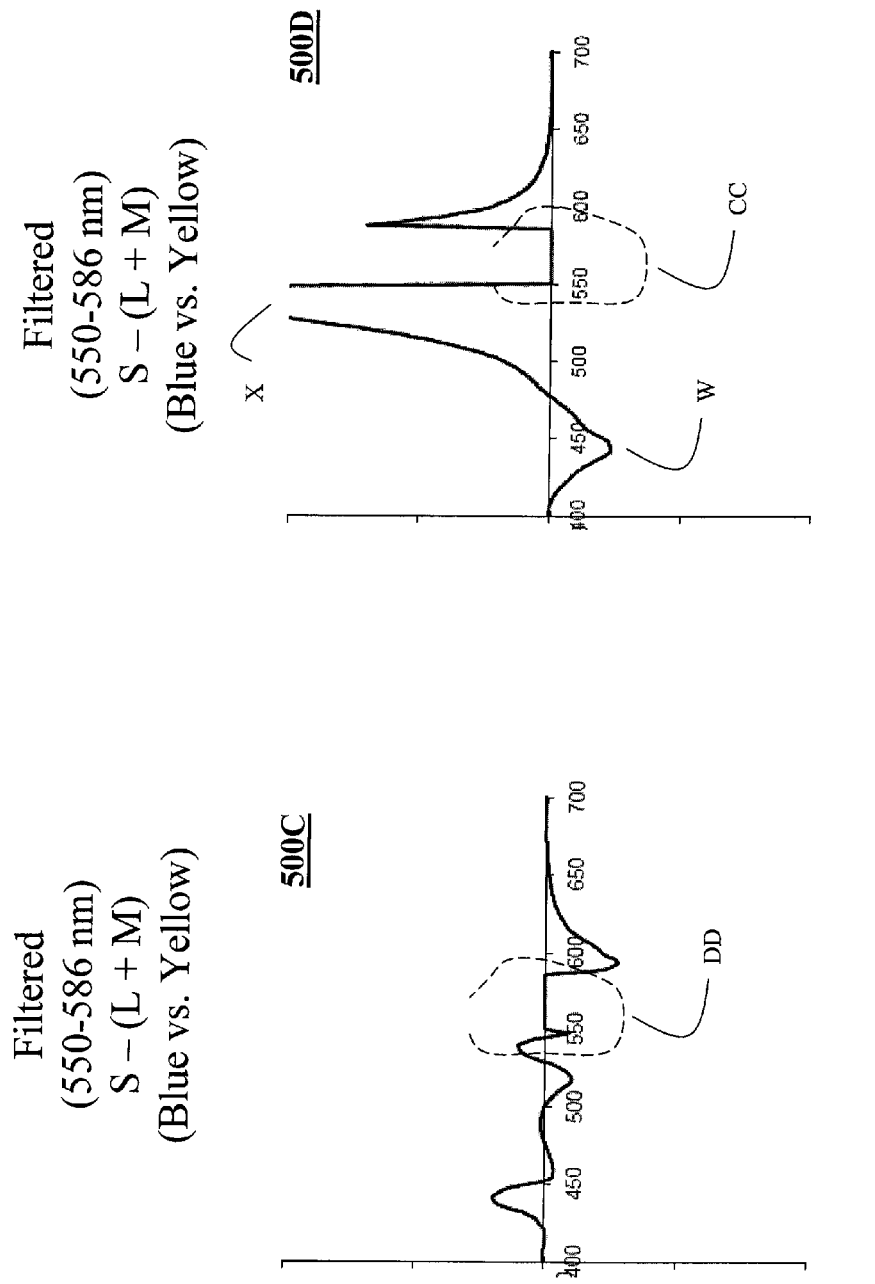
FIG. 5C is a graph illustrating the filtering of the spectral response in FIG. 5A showing the cancellation of the spectral response indicating a change in blood oxygenation, in accordance with one embodiment of the present invention.
FIG. 5D is a graph illustrating the filtering of the spectral response in FIG. 5B, in accordance with one embodiment of the present invention.

FIGS. 5C and 5D are graphs illustrating the filtered spectral responses or signatures of FIGS. 5A and 5B for high blood oxygenation and high blood volume in a skin of a human as perceived in the second human perceived chromatic channel [e.g., S−(L+M)]. As previously described, the S−(L+M) chromatic channel produces an overall response that can be used to detect blood volume. For instance, the overall response indicates a blueness that is perceived by the brain to indicate varying degrees of blood volume.

More particularly, FIG. 5D illustrates the approximate spectral response 500D as perceived by a human for skin exhibiting high blood volume. As shown, the spectral response in 500D is filtered and determined in the second chromatic channel [e.g., S−(L+M)]. Previously, in FIG. 5B, the overall response in the spectral response 500B is overwhelmingly blue, since the response curve lies mostly above the horizontal axis. Further, through the selection of the appropriate frequency range to orthogonalize signals detecting blood volume and blood oxygenation, the overall response from spectral response 500D is still primarily above the horizontal axis, with minimal interference from the yellowness exhibited at peak W. As shown in highlighted area CC of FIG. 5D, a frequency range between 550-586 is filtered out. The remaining area below peak X still generates a strong blue response indicating high blood volume.

In addition, the overall response in the second chromatic channel [e.g., S−(L+M)] may be interfered by signals present in association with the detection of blood oxygenation. FIG. 5C illustrates the approximate spectral response 500C as perceived by a human for skin exhibiting high blood oxygenation. The spectral response 500C is filtered and determined in the second chromatic channel. Previously, in FIG. 5A, at peaks P and Q, the yellow response dominates and may interfere with the overall blue response perceived by the brain in the second chromatic channel. The present invention is able to reduce the influence of the spectral response 500C that is generated from the presence of blood oxygenation in the second chromatic channel. As such, the overall response in the second chromatic channel [S−(L+M)] is used primarily to detect blood volume with minimal interference from signals associated with detection of blood oxygenation.

In FIG. 5C, by selecting the appropriate frequency range, the spectral response 500C is balanced through the removal of portions of the curve associated with peaks P and Q in FIG. 5A. That is, the area above the horizontal axis is approximately equal to the area below the horizontal axis, and thereby minimizing any effect the spectral response 500C may have on the brain when processing the overall response in the second chromatic channel [S−(L+M)]. As shown in highlighted area DD of FIG. 5C, the frequency range between 550-586 nm is filtered out, thereby balancing the spectral response 500C and minimizing its effect on the overall blue response in the second chromatic channel. In other words, the signals from the second chromatic channel generate primarily an overall blue response that is attributed mostly to blood volume. That is, the overall response from the second chromatic channel is generated from the spectral response in FIG. 5D used for detecting blood volume, with minimal interference from signals associated with detecting blood oxygenation in FIG. 5C. In that manner, an overall blue response used to detect changes in blood volume is orthogonalized from signals detecting blood oxygenation.

Figure 6B:
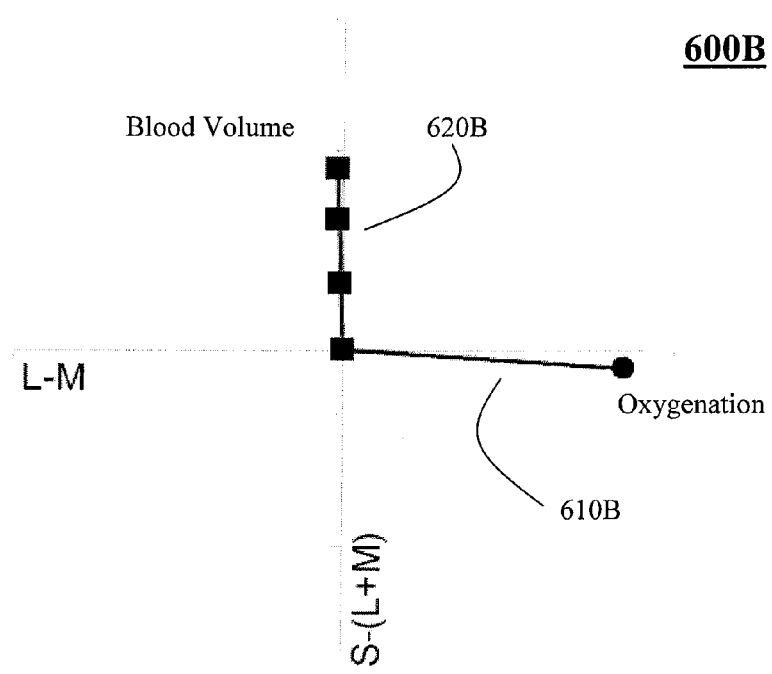
FIG. 6B is a vector graph illustrating orthogonality of signals indicting blood oxygenation and blood volume after filtration of the visible light spectrum, in accordance with one embodiment of the present invention.

FIG. 6B is a graph 600B showing vectors illustrating the overall color effect for the filtered spectrum responses used to detect both blood oxygenation and blood volume over the first (L−M) channel and the second chromatic channel [S−(L+M)]. As in FIG. 6A, the horizontal axis is used to show the red vs. green response over the first chromatic channel (L−M), where redness is associated with the right side and greenness is associated with the left side of the horizontal axis. The vertical axis is used to show the blue vs. yellow response over the second chromatic channel [S−(L+M)], where blueness is associated with the top portion and yellowness is associated with the bottom portion of the vertical axis.

For instance, vector 610B is representative of the perceived response for high blood oxygenation that is now filtered. Typically, human perception associates a strong red response with high blood oxygenation. As shown in FIG. 6B, vector 610B shows a strong red signal, primarily from the spectrum response in FIG. 4C. In comparison to the weak red response of vector 610A, the length of vector 610B is longer and of more magnitude. In addition, vector 610 lies closer to the horizontal axis, indicating less of a yellowing influence from signals in the second chromatic channel [S−(L+M)]. As such, signals from the first chromatic channel (L−M) give an overall red response that primarily indicates varying degrees of blood oxygenation.

Vector 620B is representative of the perceived response for high blood volume that is now filtered. Typically, human perception associates a strong blue response with high blood volume. As shown in FIG. 6B, vector 620B shows a strong blue signal, primarily from the spectrum response in FIG. 5D. In comparison to the mixed blue-green response of vector 620A, vector 620B lies close to the vertical axis, indicating less of the greening influence from signals in the first chromatic channel (L−M). As such, signals from the second chromatic channel [S−(L+M)] give an overall blue response that primarily indicates varying degrees of blood volume.

More particularly, vectors 610A and 620A are now orthogonal to each other. For instance, the two vectors are ninety degrees from each other. As such, an overall red response from signals in the first chromatic channel indicates blood oxygenation and an overall blue response from signals in the second chromatic channel indicates blood volume. In other words, signals used for detecting blood volume in vector 620B do not interfere and confuse the brain when detecting blood oxygenation using vector 610B. Likewise, signals used for detecting blood oxygenation in vector 610B do not interfere and confuse the brain when detecting blood volume using vector 620B.

In another embodiment, an apparatus for detecting changes in skin color is capable of orthogonalizing signals detecting blood oxygenation and blood volume. The apparatus includes means for selecting a light condition, wherein the light condition is associated with a spectral power distribution. Means for determining a first plurality of spectral responses for a first human perceived chromatic channel is included. The first plurality of spectral responses primarily detects blood oxygen concentration, but can pick up responses from blood volume in a skin of a human in response to and as stimulated or illuminated by the spectral power distribution. Means for determining a second plurality of spectral responses for a second human perceived chromatic channel is included. The second plurality of spectral responses primarily detects blood volume, but can pick up responses from blood oxygenation, in response to or as illuminated by the spectral power distribution. Means for isolating a frequency range is included that filters frequencies in the first and second plurality of spectral responses. The filtering accentuates the blood oxygenation with a first perceived color (e.g., red) and the blood volume with a second perceived color (e.g., blue).

In another embodiment, one or more filters are proposed. For instance, one or more filters filtering one or more frequency ranges is contemplated to orthogonalize signals detecting blood oxygenation and blood volume. In addition, in other embodiments, a multi-filter setup is contemplated, in which one filter for orthogonalizing signals detecting blood oxygenation and blood volume is added to a substrate or carrier that also have some other kind of useful filter (e.g., notch filter) in place. For example, the second filter may be an anti-UV (ultraviolet) notch filter coating, for blocking electromagnetic radiation in the ultraviolet band, approximately 300-400 nm. Another example of a second filter is the well-known "blueblocker" notch filter coating (approximately 300-500 nm).

Figure 8A:
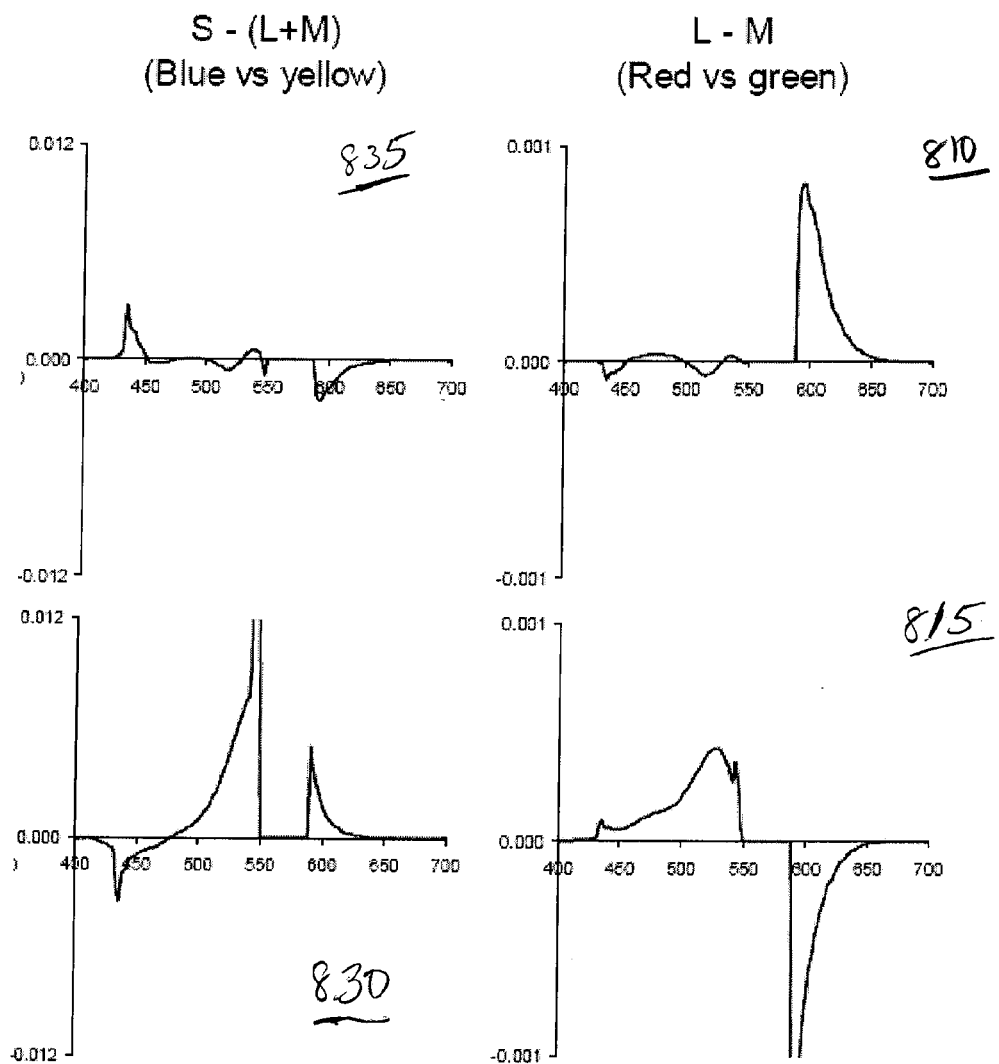
FIG. 8A illustrates a series of spectral responses determined for the F1 illuminant in which the frequency range of 550-586 nm is filtered, in accordance with one embodiment of the present invention.

FIG. 8A illustrates a series of spectral responses determined for the F1 illuminant in which the frequency range of 550-586 nm is filtered, in accordance with one embodiment of the present invention. Approximate spectral responses for high blood oxygenation and high blood volume in skin are shown for both a first chromatic channel (L−M) and a second chromatic channel [S−(L+M)]. All of the spectral responses are filtered between 550 nm and 586 nm. As a result, the overall red response over the L−M channel is contributed mostly by graph 810, and the response curve 815 is minimized through balancing, as previously described. As a result, the overall red response in the L−M channel is used for detecting blood oxygenation, with minimal interference from signals associated with blood volume. Correspondingly, the overall blue response over the [S−(L+M)] channel is contributed mostly by graph 830, and the response curve 835 is minimized through balancing, as previously described. As a result, the overall blue response from the [S−(L+M)} channel is used for detecting blood volume, with minimal interference from signals associated with blood oxygenation.

Figure 8B:
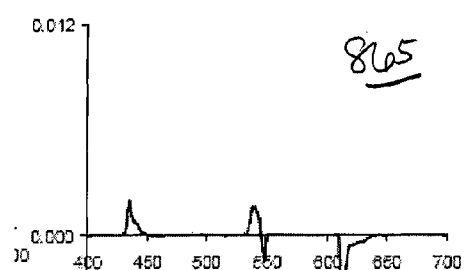
FIG. 8B illustrates a series of spectral responses determined for the F12 illuminant in which the frequency range of 550-610 nm is filtered, in accordance with one embodiment of the present invention.
Figure 8B:
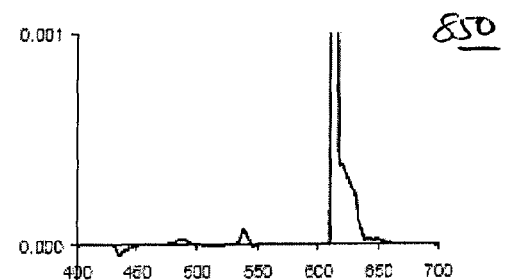
Figure 8B:
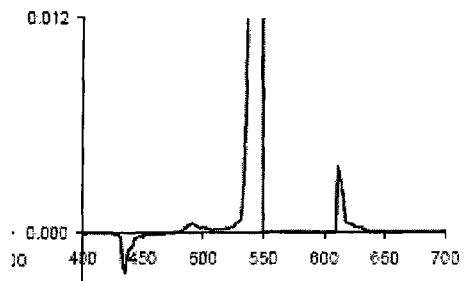
Figure 8B:
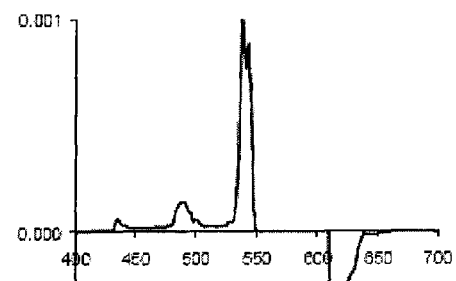

FIG. 8B illustrates a series of spectral responses determined for the F12 illuminant in which the frequency range of 550-610 nm is filtered, in accordance with one embodiment of the present invention. Approximate spectral responses for high blood oxygenation and high blood volume in skin are shown for both a first chromatic channel (L−M) and a second chromatic channel [S−(L+M)]. All of the spectral responses are filtered between 550 nm and 610 nm. As a result, the overall red response over the L−M channel is contributed mostly by graph 850, and the response curve 855 is minimized through balancing, as previously described. As a result, the overall red response in the L−M channel is used for detecting blood oxygenation, with minimal interference from signals associated with blood volume. Correspondingly, the overall blue response over the [S−(L+M)] channel is contributed mostly by graph 860, and the response curve 865 is minimized through balancing, as previously described. As a result, the overall blue response from the [S−(L+M)] channel is used for detecting blood volume, with minimal interference from signals associated with blood oxygenation.

Figure 9:
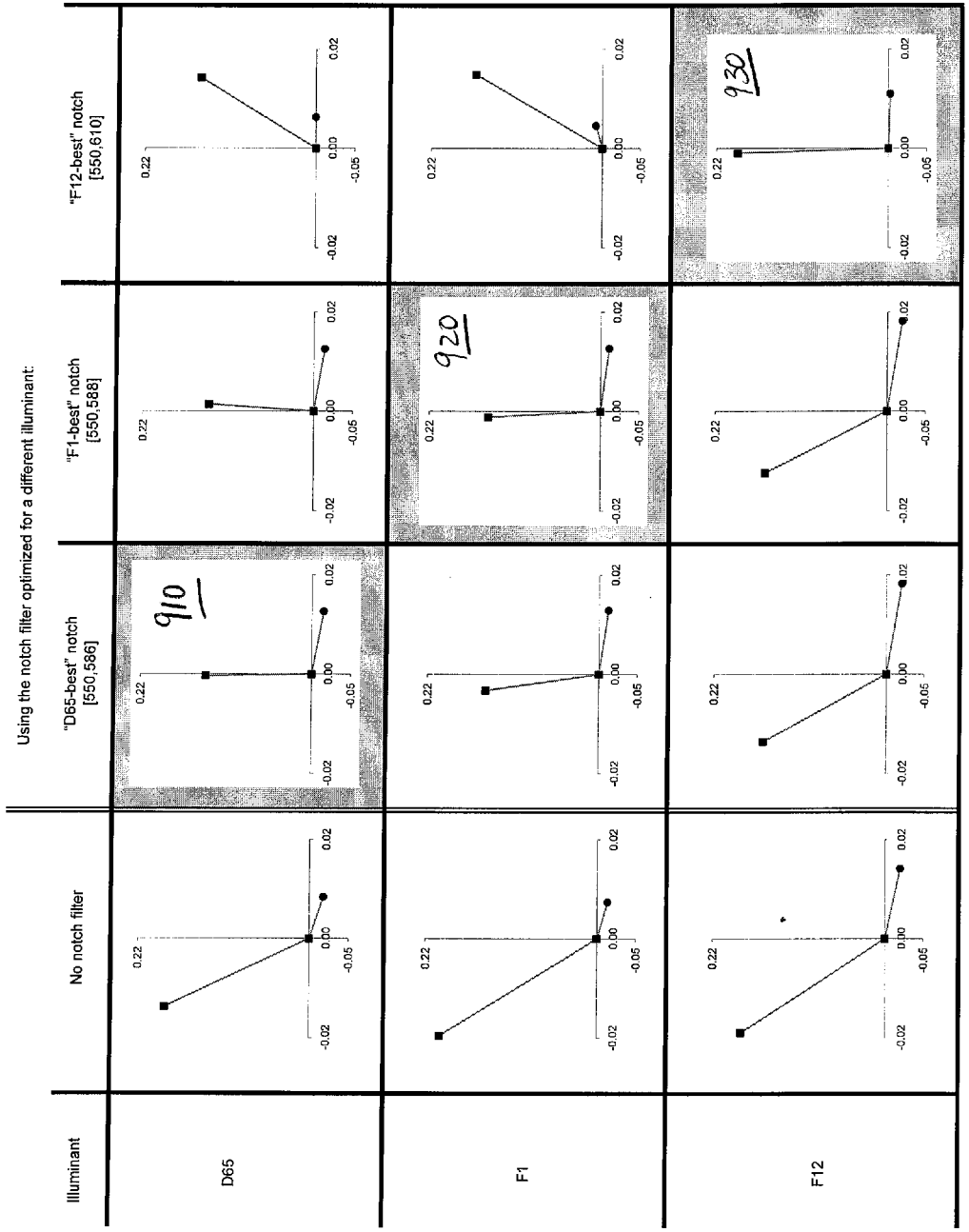
FIG. 9 illustrates various vector graphs illustrating various filter ranges used to orthogonalize signals indicating oxygen concentration form hemoglobin and blood volume under various lighting conditions, in accordance with embodiments of the present invention.

FIG. 9 illustrates various vector graphs illustrating various filter ranges used to orthogonalize signals indicating oxygen concentration form hemoglobin and blood volume under various lighting conditions, in accordance with embodiments of the present invention. Vector responses for three lighting illuminants corresponding to D65 illuminant, F1 illuminant, and F12 illuminant are shown. In particular, the vector responses are indicative of the overall color effect for the filtered spectrum response used to detect both blood oxygenation and blood volume over the first (L−M) channel and the second chromatic channel [S−(L+M)]. Various filter ranges are contemplated, such as no filtering, and filtering between 550-586, between 550-588, and between 550-610. As in FIGS. 6A and 6B, in each vector graph, the horizontal axis is used to show the red vs. green response over the first chromatic channel (L−M), where redness is associated with the right side and greenness is associated with the left side of the horizontal axis. The vertical axis is used to show the blue vs. yellow response over the second chromatic channel [S−(L+M)], where blueness is associated with the top portion and yellowness is associated with the bottom portion of the vertical axis.

In general, the problematic band removed by a filter (e.g., a notch filter) according to embodiments of the invention lies within the range 550-620 nm, and depends upon the illuminant incident on the skin, in embodiments of the present invention. The frequency range filters out the narrow ranges where signals indicative of blood oxygenation or blood volume reflect wavelengths that (when visible) tend to cause the eye to perceive the "wrong color". For any reasonable illuminant, the notch best suited to perceiving the wrong color falls somewhere in the range 550 nm to 620 nm. Optimization of the edges of the notch filter is nontrivial because two signals (indicative of blood oxygenation and blood volume) need to be optimized at the same time, and the eye itself is complex in the way it maps RGB (red green blue) to perceived color.

Under standard daylight (so-called illuminant D65), a solution exists for a frequency range between 550-586 nm, in one embodiment. This is shown in graph 910 of FIG. 9. In another embodiment, a solution exists for a frequency range between 570-585 nm. Of course, other frequency ranges are contemplated. Under fluorescent lighting, varying solutions exist for isolating a frequency range depending upon the spikes in the corresponding power spectrum in various embodiments, such as 570-585 nm, 550-586 nm, and 550-616 nm. In particular, for F1 illuminant a frequency range of 550-588 is isolated for filtering, as is shown in graph 920 of FIG. 9, in one embodiment. For the F12 illuminant, a frequency range of 550-610 is isolated for filtering, in another embodiment. Of course, other frequency ranges are contemplated. For individuals with deuteranomalous colorblindness, one possible solution is to filter a frequency range between 570-585 nm. Of course, other frequency ranges are contemplated. In one advantageous embodiment, a filter is used for blocking light from about 555 nm to 585 nm, which is optimal for general purpose (indoor and outdoor) use.

Note in the above described ranges, the exact endpoint of each range is approximate, but very likely correct to within approximately plus or minus 10 nm. As a result, in each of the vector graphs showing a suitably filtered frequency range for a given illuminant, the overall red response in the L−M channel is orthogonalized to the overall blue response from the [S−(L+M)] channel. As a result, in each case the overall red response from the L−M channel is used for detecting blood oxygenation with minimal interference from signals associated with blood volume. Also, the overall blue response from the [S−(L+M)] channel is used for detecting blood volume, with minimal interference from signals associated with blood oxygenation.

In one implementation, embodiments of the present invention allow for detecting changes in emotional state and changes in health. For instance, one application is to give a user an advantage over competitors in situations where detecting changes of emotion (anger, arousal, fear, fatigue, jealousy, etc.) may be crucial to the user's success. Such situations include dating, business/political negotiation, police/military interrogations, polygraph examinations, and poker games. Another intended application is to use the invention to give the user heightened awareness of changes in medical condition (health) of others. For example, this may be of use in hospitals. Without loss of generality, such filters could be combined with UV blocking or with other dimming or reflective coatings typically used on modern eyeglasses or sunglasses.

Figure 10:
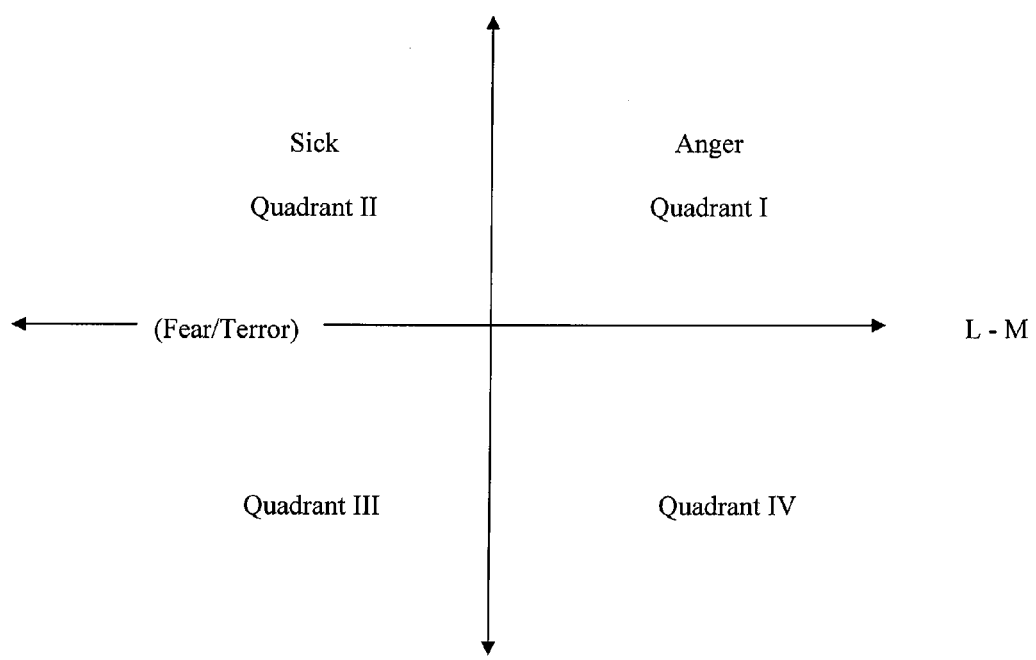
FIG. 10 is a vector graph 1000 that shows areas in which an overall color effect as perceived by a human can be used to determine the health and well being of a person, in accordance with one embodiment of the present invention.

FIG. 10 is a vector graph 1000 that shows areas in which an overall color effect as perceived by a human can be used to determine the health and well being of a persons, in accordance with one embodiment of the present invention. In addition, the vector graph 10000 could indicate an emotional state of a person. As in FIGS. 6A, 6B, and 9, the horizontal axis is used to show the red vs. green response over the L−M channel. Also, the vertical axis is used to show the blue vs. yellow response over the S−(L+M) channel. By combining the vectors corresponding to the L−M response with the vector for the S−(L+M) response, a single vector is generated that projects somewhere within the vector graph 1000. The vector response is modulated due to the filtering of the suitable frequency range for a particular illuminant. Depending on the location of the quadrant the modulated vector as projected will give an indication (due to the overall combined color response) as to the physical state of the subject under scrutiny.

For instance, along the horizontal axis giving an L−M response, a positive reading indicates that the subject is stronger, or has more energy. Also, a negative reading indicates that the subject is weaker. For the vertical axis giving an S−(L+M) response, a positive reading indicates that the subject is more lethargic, such as in the case where blood flow is slowed so that the blood volume pools at the extremities. Thus, a positive reading on the vertical axis indicates deactivation of blood volume, and a negative reading on the vertical axis indicates activation of blood.

Emotions could be interpolated from the vector reading provided in FIG. 10. For instance, an overall vector response that lies in Quadrant I corresponds to a combination of redness and blueness, shows that the subject is strong with deactivated blood, and could indicate that the subject is exhibiting anger. Also, an overall vector response that lies in Quadrant II corresponds to a combination of greenness and blueness, shows that the subject is weak with deactivated blood and could indicate that the subject is sick. Further, an overall vector response that lies near the horizontal axis in the negative region shows generally that the that the subject is weak, and could indicate that the subject is exhibiting fear or terror. An overall vector response that lies in Quadrant IV corresponds to a combination of redness and yellowness, shows that the subject is strong with activated blood, and could indicate that the subject is exhibiting anger.

While the methods of embodiments illustrated in flow diagrams of FIGS. 2 and 3 show specific sequences and quantity of operations, the present invention is suitable to alternative embodiments. For example, not all the operations provided for in the methods presented above are required for the present invention. Furthermore, additional operations can be added to the operations presented in the present embodiments. Likewise the sequences of operations can be modified depending upon the application.

An apparatus and method for detecting changes in blood volume and oxygen concentration from hemoglobin by filtering a frequency range of the visible light spectrum in order to orthogonalize human perceived signals detecting changes in blood volume and oxygen concentration in hemoglobin found in blood is thus described. While the invention has been illustrated and described by means of specific embodiments, it is to be understood that numerous changes and modifications may be made therein without departing from the spirit and scope of the invention as defined in the appended claims and equivalents thereof. Furthermore, while the present invention has been described in particular embodiments, it should be appreciated that the present invention should not be construed as limited by such embodiments, but rather construed according to the below claims.

What is claimed:

1. A method of providing a filter for detecting changes in color of human skin, comprising:
    selecting a light condition, wherein said light condition is associated with a spectral power distribution;
    determining a first plurality of spectral responses for a user that result from a change in blood oxygenation in the human skin as illuminated by said spectral power distribution;
    determining a second plurality of spectral responses for the user that result from a change in an amount of blood volume in the human skin as illuminated by said spectral power distribution;
    isolating a frequency range to be filtered by said filter, the isolated frequency range selected such when the isolated frequency range is filtered by said filter, the first plurality of spectral responses is detected by a first chromatic channel for the user and the second plurality of spectral responses is detected by a second chromatic channel for the user, wherein the two chromatic channels are orthogonal to minimize the interference between the first and second plurality of spectral responses, and each chromatic channel is adapted for the user perception by L-cones, M-cones, S-cones or any combination thereof; and
    providing said filter that is configured to allow the user to detect changes in color of the human skin based on the isolated frequency range without the use of computer processing equipment, said filter comprising a carrier.

2. The method of claim 1, wherein said filter is a notch filter that filters said isolated frequency range.

3. The method of claim 1, wherein said first plurality of spectral responses comprise an overall red response as a first perceived color that indicates blood oxygenation, wherein the second plurality of spectral responses comprise an overall blue response as a second perceived color that indicates blood volume.

4. The method of claim 3, wherein the first chromatic channel is an L−M chromatic channel.

5. The method of claim 4, wherein the second chromatic channel is an S−(L+M) chromatic channel.

6. The method of claim 1, wherein said selecting a light condition comprises:
    selecting a light condition, that approximates that of an illuminant consisting essentially of:
    standard illuminant D65; and
    illuminant F-1.

7. The method of claim 1, wherein said isolated frequency range is between 555-585 nanometers.

8. The method of claim 1, wherein isolating a frequency range comprises isolating a frequency range of 525 nm to 590 nm to be passed through said filter, said passing through light being associated with changes in blood volume.

9. The method of claim 1, wherein isolating a frequency range comprises isolating a frequency range of 525 nm to 590 nm to be blocked by said filter, said blocked light being associated with changes in blood oxygenation.

10. The method of claim 1, wherein isolating a frequency range comprises isolating a frequency range of 500 nm to 530 nm, of 570 nm to 584 nm, or both to be blocked by said filter, said blocked light being associated with changes in blood oxygenation.

11. A method for detecting changes in color of human skin, comprising:
providing a filter according to the method of claim 1;
receiving, by said filter, unfiltered light from a light source as an input;
filtering, through said filter, the isolated frequency range of the unfiltered light to produce filtered light;
outputting, from said filter, the filtered light for allowing a user viewing the human skin in said filtered light to be able to distinguish between a change in color of the human skin based on blood oxygenation and a change in color of the human skin based on blood volume.

12. The method of claim 11, wherein said receiving unfiltered light further comprises: receiving said unfiltered light from said light source, and wherein said outputting of said filtered light comprises outputting said filtered light as ambient light.

13. The method of claim 11, wherein said filter is on a lens.

14. The method of claim 13, wherein said lens receives said filtered light reflecting off skin of the human.

15. The method of claim 11, wherein filtering a frequency range of said unfiltered light comprises passing through the unfiltered light within a frequency range of 525 nm to 590 nm, said filtered light being associated with changes in blood volume.

16. The method of claim 11, wherein filtering a frequency range of said unfiltered light comprises blocking the unfiltered light within a frequency range of 525 nm to 590 nm, said filtered light being associated with changes in blood oxygenation.

17. The method of claim 11, wherein filtering a frequency range of said unfiltered light comprises blocking unfiltered light within a frequency range of 500 nm to 530 nm, of 570 nm to 584 nm, or both, said filtered light being associated with changes in blood oxygenation.

18. The method of claim 11, wherein the frequency range is between 550-586 nm.

19. The method of claim 11, wherein the frequency range is between 570-585 nm.

* * * * *